(12) United States Patent
Marinello

(10) Patent No.: US 6,725,086 B2
(45) Date of Patent: Apr. 20, 2004

(54) METHOD AND SYSTEM FOR MONITORING SEDATION, PARALYSIS AND NEURAL-INTEGRITY

(75) Inventor: Stephen Marinello, Beverly, MA (US)

(73) Assignee: Draeger Medical Systems, Inc., Danvers, MA (US)

( * ) Notice: Subject to any disclaimer, the term of this patent is extended or adjusted under 35 U.S.C. 154(b) by 21 days.

(21) Appl. No.: 09/991,360

(22) Filed: Nov. 20, 2001

(65) Prior Publication Data

US 2002/0095098 A1 Jul. 18, 2002

Related U.S. Application Data

(60) Provisional application No. 60/262,179, filed on Jan. 17, 2001.

(51) Int. Cl.[7] .............................................. A61B 5/0484
(52) U.S. Cl. ....................................................... 600/544
(58) Field of Search ........................ 607/1, 2; 600/544, 600/545, 546

(56) References Cited

U.S. PATENT DOCUMENTS

| | | | |
|---|---|---|---|
| 3,850,161 A | 11/1974 | Liss | 128/2.1 |
| 3,880,144 A | 4/1975 | Coursin et al. | 128/2.1 |
| 4,390,023 A | 6/1983 | Rise | 128/421 |
| 4,515,169 A | 5/1985 | Ward | 128/746 |
| 4,535,185 A | 8/1985 | Thoma | 564/242 |
| 4,869,264 A | 9/1989 | Silberstein | 128/731 |
| 5,131,401 A | 7/1992 | Westenskow et al. | 128/741 |
| 5,195,531 A | 3/1993 | Bennett | 128/733 |
| 5,263,490 A | 11/1993 | Hayes et al. | 128/741 |
| 5,295,491 A | 3/1994 | Gevins | 128/731 |
| 5,549,118 A | 8/1996 | John et al. | 128/731 |
| 5,549,656 A | 8/1996 | Reiss | 607/48 |
| 5,566,678 A | 10/1996 | Cadwell | 128/731 |
| 5,614,887 A | 3/1997 | Buchbinder | 340/573 |
| 5,699,808 A | 12/1997 | John | 128/731 |
| 5,846,208 A | 12/1998 | Pichlmayr et al. | 600/544 |
| 5,913,882 A | 6/1999 | King | 607/62 |
| 6,052,619 A | 4/2000 | John | 600/544 |
| 6,185,451 B1 | 2/2001 | Richardson et al. | 600/546 |

Primary Examiner—Scott M. Getzow
(74) Attorney, Agent, or Firm—Jack Schwartz & Assoc.

(57) ABSTRACT

The present invention relates to a method and system in which a small stimulator unit which is designed to be mounted near the patient. A single cable connects the stimulator unit to the patient monitor. This cable both provides power to the stimulator unit, as well as 2-way data communication between the stimulator unit and the patient monitor. The patient monitor provides the user interface for the present invention, as well as other parameters such as heart rate and blood pressure.

39 Claims, 1 Drawing Sheet

METHOD AND SYSTEM FOR MONITORING SEDATION, PARALYSIS AND NEURAL-INTEGRITY

This is a nonprovisional application of provisional application Ser. No. 60/262,179 by Stephen A. Marinello filed Jan. 17, 2001.

BACKGROUND OF THE INVENTION

1. Field of the Invention

The present invention relates a method and a system for monitoring sedation, paralysis and neural integrity as is required in surgical and intensive care environments. In particular the present invention relates to a compact and affordable method and system for monitoring these parameters.

2. Field of the Invention

In the course of their practice, Anesthesiologist must monitor the effects of the agents they administer to their patients, and the effects of various surgical manipulations, to ensure the well being of their patients. Three important categories which require diligent monitoring from the anesthesiologist are as follows:

Sedation

Sedatives are administered to render a patient unconscious, prevent stress to the Central Nervous System, and eliminate pain. Care must be taken to avoid over-sedating, which wastes expensive anesthetic, delays patient recovery, and may contribute to other long-term effects including coma. Under-sedating is also a serious problem, which may cause patients to awaken during the procedure. Continual assessment of the correct level of sedation is therefore necessary. Anesthesiologist normally rely on clinical signs such as heart rate or blood pressure responses to surgical stimuli to ensure the adequacy of sedation, but these signs are not present in certain surgical procedures, such as heart bypass surgery, leaving the anesthesiologist without any measure of sedation. A patient's electroencephalogram (EEG) may provide additional information, but the completed interpretation of raw EEG requires expert training. Parameters derived from the EEG such as Median Frequency or Bispectral Index may help in the interpretation, but these have not been found to be totally reliable in all cases. Derived parameters may be susceptible to artifact or noise; have varying responses with different agents; and provide no objective feedback to the clinicians when the data they are presenting is erroneous.

Mid-latency Auditory Potentials (MLAEP) have been proposed as a method to determine sedation which overcomes the difficulties seen with raw EEG and derived EEG parameters. MLAEP is obtained by recording the EEG while auditory tones are issued to the patient via headphones, and applying signal processing techniques to remove all but those signals which are correlated to the tone, so that over time, a waveform is generated. MLAEP has been shown to give a graded response to level of sedation, insensitive to different sedative agents. Artifact removal is proportional to the time average, so that arbitrarily clean signals may be obtained. The generated waveform may be inspected for accuracy, giving immediate confirmation that the data is accurate.

Neuromuscular Blockade

Neuromuscular blockage agents are given to induce temporary paralysis, allowing surgical manipulation without patient movement, either voluntary or involuntary. It is important that the paralysis is maintained throughout surgery, to prevent movement which might interfere with the surgeon. As each patient responds differently to the agents, monitoring of the effect is necessary to establish when a patient may be safely extubated.

A subjective indication of paralysis may be obtained by using a nerve stimulator—a nerve such as the ulnar nerve is stimulated at the wrist, and the thumb response is observed. However, this method is not easily quantifiable, and the documentation must be done manually. An improved variant of this technique utilizes a method of measuring the thumb response directly, and performing calculations on this response to determine paralysis. Parameters such as Train-of-Four Percentage (TOF %) measure the ratio of the 4th to the 1st response, and Post-tetanic Count (PTC), count the number of responses which can be induced following tetanus. These parameters are objective, convenient to obtain, and may be documented automatically.

Neural Integrity

Certain surgical procedures such as spinal surgery may compromise the integrity of motor and sensory nerve pathways. Any surgery on or near the spine may damage the spinal cord, and any damage must be detected as soon as possible to prevent permanent injury. A standard procedure to attempt to detect any damage is to partially waken the patient, and instruct him/her to "wiggle your toes" upon command. This technique is slow, delaying the surgery and only gives sporadic, subjective measures of pathway integrity.

A superior method which gives continuous, objective measures is to use Somatosensory Evoked Potentials (SEP). Any electric stimulus is applied to a sensory nerve, such as the Radial nerve, and a response is observed in the patients EEG. Signal processing techniques similar to the MLAEP are performed to obtain a waveform of brain patterns correlated to the stimulus. Changes in the shape or latency (time delay since stimulus) give a graded indication of integrity. The brain response to a single stimulus from 2 different locations given an indication of propagation delay, providing an early indication of any injury.

Despite the availability of devices to facilitate continuous, objective monitoring as described above, such monitoring is not performed in every institution, or in every surgical case, because of the following problems:

Expense of the devices. Currently, 2 or 3 different devices are required to provide the full range of monitoring required. These devices are expensive, some costing $20,000 to $100,000. Thus a hospital may purchase a few devices for an entire surgical floor to share among many operating rooms, limiting their widespread use.

Inconvenience of use. These devices each require their own application to the patient, with associated sensors. The task of attaching the different sensors and probes may take 30 minutes or more. Each has its own interface to the clinician, and must be positioned in the crowded workspace of the Operating Theatre. Many cables must be run from the patient to the anesthesia station, crowding the workspace, increasing electrical noise, and risking accidental disconnection.

Complexity of use. These devices are usually adapted from the related diagnostic applications, and are poorly adapted to the monitoring application. In particular, the user interfaces are not optimized for ease of use in the surgical setting. The anesthesiologist is required to learn several different interfaces. Therefore it would be desirable to provide a method and system for monitoring these parameters which overcomes the aforementioned drawbacks of the prior art proposals.

SUMMARY OF THE INVENTION

The present invention provides a method and a system for integrating all of these anesthesia monitoring functions into a single module, which has the advantages of small size, low cost, ease-of-use, minimal cabling, and integration into a single user-interface at the anesthesiologist's monitor in which a small stimulator unit which is designed to be mounted near the patient. A single cable connects the stimulator unit to the Patient Monitor. This cable both provides power to the stimulator unit, as well as 2-way data communication between the stimulator unit and the Patient Monitor. The Patient Monitor provides the user interface for the present invention, as well as other parameters such as Heart Rate, Blood Pressures, etc.

BRIEF DESCRIPTION OF THE DRAWINGS

The invention will be described in more detail in the following description of preferred embodiments with reference to the following figures in which.

DETAILED DESCRIPTION OF THE PREFERRED EMBODIMENTS

Figure 1:
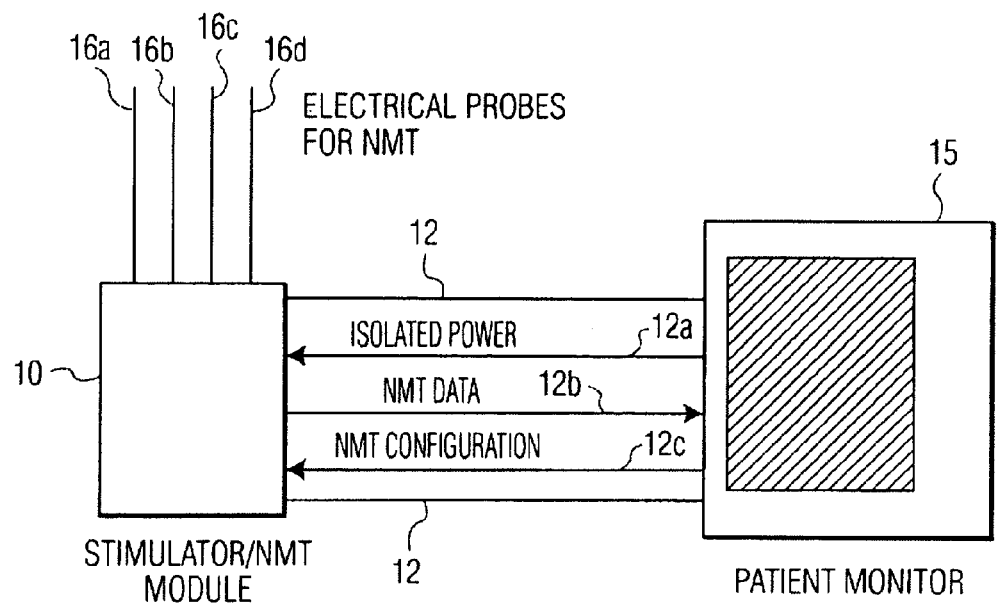
FIG. 1 is a block diagram of a first embodiment of the present invention.

Referring now to the drawings and in particular FIG. 1 which illustrates a first embodiment of the present invention which includes a small stimulator unit 10 which is designed to be mounted near the patient. A single cable 12 connects the stimulator unit 10 to the Patient Monitor 15. This cable 12 both provides power (12A) to the stimulator unit 10, as well as 2-way data communication (12B, 12C) between the stimulator unit 10 and the Patient Monitor 15. The Patient Monitor 15 provides the user interface for the invention, as well as other parameters such as heart rate, blood pressures, etc.

In the embodiment of FIG. 1, as described above, the anesthesiologist may monitor only Neuromuscular Transmission (NMT). In this embodiment no EEG module is connected to the system. A single cable is connected between the stimulator unit and the patient, which terminates as the patient end in 4 probes (16a–d): 2 electrical connections (16a, 16b) for administering the electrical stimuli, an accelerometer (16c) for measuring the twitch response, and a probe (16d) which records skin temperature. Information from the stimulator unit 10 to the Patient Monitor (FIG. 12A) includes NMT Data (12b) which is neuromuscular transmission data. Data from the Patient Monitor 15 to the stimulator module or unit 10 along cable 12 includes NMT configuration data (12,c see FIG. 12B) to the stimulator/NMT module 10. This stimulator unit (10) reports the NMT-only configuration to the Patient Monitor (15), which enables only the NMT configuration menus, simplifying the user interface. Commands (12c) are then sent from the Patient Monitor (15) to the stimulator unit (10) to start or stop NMT measurements, and to adjust the configuration. Parameters, technical conditions and waveforms are sent from the stimulator unit (10) to the Patient Bedside (not shown but connected to probes (16a–d) for display, trending, sounding of appropriate alarms, printing, and networking to other devices.

Alternatively for embodiments of the present invention such as the embodiment of FIG. 1, described above and for the embodiment of FIG. 2, described below, the stimulator unit 10 can be formed of one or more separate units (not shown), each unit serving a different stimulus modality e.g. auditory stimulus, electrical stimulus or being located at a different body location, e.g. auditory stimulus or electrical stimulus for different body parts. These stimulator units can share data, power and trigger signals on a single cable line such as cable line 12 shown in FIG. 1.

Figure 2:
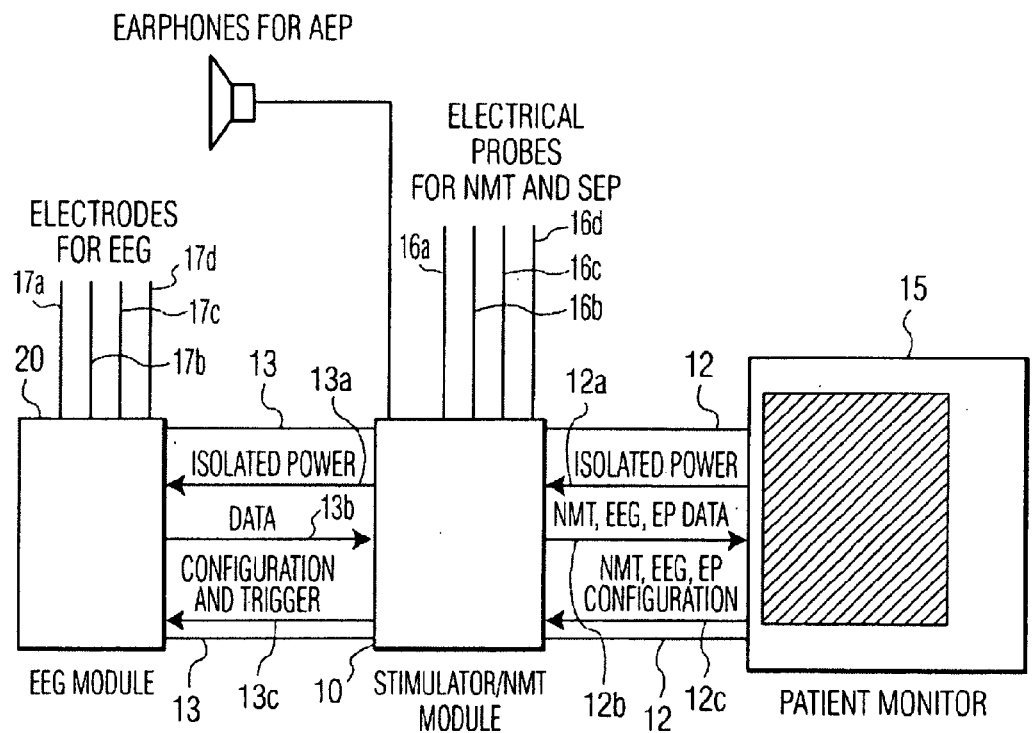
FIG. 2 is a block diagram of a second embodiment of the present invention in which an EEG Module is connected to the Stimulator unit.

FIG. 2 of the drawings illustrates a second embodiment of the invention in which an EEG module or pod (20) is connected to the stimulator unit (10). This embodiment provides for monitoring of NMT, SEP and EEG signals. In this embodiment cable 12 again provides isolated power from the Patient Monitor 15 to the stimulator/NMT module 10 as well as a 2 way communication between the stimulator/NMT module (10) and the Patient Monitor 15.

The EEG module (20) is connected to the stimulator/NMT module 10 by a cable 13 which provides for a isolated power between the stimulator/NMT module 10 and the EEG module 20 as well as two way communication between the stimulator/NMT module 10 and the EEG module 20 where data is provided from the EEG module 20 to the stimulator module/NMT module 10 and configuration and a trigger 13c is sent from the stimulator/NMT module (10) to the EEG Module (20).

Information from the stimulator/NMT module 10 to the Patient Module (20) includes NMT, EEG and EP data. The stimulator/NMT module (10) receives EEG data from the EEG module 20. The Patient Monitor 15 sends data to the stimulator/NMT module 10 along cable 12. The Patient Module 15 provides NMT, EEG, EP configurations to the stimulator/NMT module 10 along cable 12.

The EEG module 20 includes electrodes 17a–d for monitoring a patient's EEG so that EEG data can be sent along cable 13 to the stimulator module 10 and then sent from the stimulator unit 10 to the patient monitor through cable 12. A configuration for the EEG can be transmitted from the Patient Monitor 15 to the stimulator module 10 and from the stimulator module 10 to the EEG Module 20.

Whenever the SEP or AEP is enabled, the Patient Monitor 15 determines the firing time of the auditory and electrical stimulators. If necessary, it interleaves the stimulus times to prevent overlapping the brain responses. It also randomly adjusts the time intervals to prevent late brain responses from contaminating the early portion of following stimuli. The requested firing time, and the identifier of which stimulator is to fire, is transmitted from the Patient Monitor 15 to the stimulator module 10 and to the EEG module 20. The stimulator module 10 will issue the stimulus at the requested time, and the EEG module 20 begins acquiring the requested Evoked Potential. This is possible because of the synchronized clock shares by all 3 units.

Alternatively, the EEG module 20 may take the role of the Patient Monitor in the above description, and issue commands directly to the stimulator module 10 instead (not shown).

Another alternative trigger modality is for the stimulator module to send the trigger information over a fiber-optic conduit to the EEG Module 20. A time trigger is sent first, following by an encoded stimulator identifier (not shown).

Whenever an EEG channel is configured to measure SEP or AEP, it is also possible to display the spontaneous EEG and the associated parameters from that same lead derivation. This is selectable from the Patient Monitor 15.

While certain embodiments have been shown and described, it is distinctly understood that the invention is not limited thereto but may be otherwise embodied within the scope of the appended claims.

What is claimed is:

1. An adaptive system for monitoring neurological electrical activity, comprising:
   an electrical stimulation signal generator;
   an acoustic stimulation signal generator;
   a conditioning network for coupling to electrodes and for conditioning electrical signals received via electrodes, said electrical signals representing neurological electrical activity at least partially generated in response to at least one of (a) electrical muscular stimulation and (b) said acoustic stimulation; and
   a processing network adaptively configured for processing conditioned electrical signals derived from neurological activity in response to said electrical muscular stimulation differently to electrical signals derived in response to said acoustic stimulation.

2. The adaptive system according to claim 1 wherein said electrical stimulation signal generator is formed of one or more separate units and each of said units serves a different stimulus modality.

3. The adaptive system according to claim 1 wherein said electrical stimulation signal generator is formed of one or more separate units and each of said units is located to provide stimulus for a different body location.

4. The adaptive system according to claim 1 wherein said acoustic stimulation signal generator is formed of one or more separate units and each of said units serves a different stimulus modality.

5. The adaptive system according to claim 1 wherein said acoustic stimulation signal generator is formed of one or more separate units and each of said units is located to provide stimulus for a different body location.

6. The adaptive system according to claim 1, wherein said adaptive system also monitors neuromuscular activity and
   said conditioning network conditions electrical signals representing muscular activity,
   said processing network is adaptively configured for processing conditioned electrical signals derived by electrical stimulation of muscle.

7. The adaptive system according to claim 1 wherein said electrical stimulation signal generator is a single electrical stimulation signal generator for monitoring both neuromuscular transmission monitoring and somatosensory evoked potential.

8. The adaptive system according to claim 1 wherein said electrodes are a single pair of electrodes for monitoring both NMT and SEP.

9. The adaptive system according to claim 1 wherein said probes are a single pair of stimulator probes to evoke SEP and NMT signals either independently or concurrently.

10. The adaptive system according to claim 1 wherein said electrodes coupled to said conditioning network are a single pair of electrodes for monitoring muscle and neurological electrical activity of a patient.

11. An adaptive system for monitoring neurological electrical activity, comprising:
    an electrical stimulation signal generator;
    an acoustic stimulation signal generator;
    a conditioning network for coupling to electrodes and for conditioning electrical signals received via electrodes, said electrical signals representing neurological electrical activity at least partially generated in response to at least one of (a) electrical muscular stimulation and (b) said acoustic stimulation; and
    a processing network adaptively configured for processing conditioned electrical signals derived from neurological activity in response to said electrical muscular stimulation differently to electrical signals derived in response to acoustic stimulation,
    wherein said adaptive system is adapted to auto-configure itself for at least one of (a) neuromuscular transmission monitoring (b) somatosensory evoked potential stimulation and (c) auditory evoked potential stimulation when connected to an EEG module and to a neuromuscular transmission monitoring device only when not connected to said EEG module.

12. An adaptive system for monitoring neurological electrical activity, comprising:
    an electrical stimulation signal generator;
    an acoustic stimulation signal generator;
    a conditioning network for coupling to electrodes and for conditioning electrical signals received via electrodes, said electrical signals representing neurological electrical activity at least partially generated in response to at least one of (a) electrical muscular stimulation and (b) said acoustic stimulation;
    a processing network adaptively configured for processing conditioned electrical signals derived from neurological activity in response to said electrical muscular stimulation differently to electrical signals derived in response to acoustic stimulation; and
    a digital serial interface for sending trigger information from an evoked potential stimulator to an EEG device for synchronization with a spontaneous EEG signal.

13. The adaptive system according to claim 12 further comprising a single trigger line for transmitting a combined time-of-occurrence and ID code in order to differentiate among different stimulation modes or sites when triggering an EEG device.

14. An adaptive system for monitoring neurological electrical activity, comprising:
    an electrical stimulation signal generator;
    a conditioning network for coupling to electrodes and for conditioning electrical signals received via electrodes in response to said electrical stimulation, said electrical signals representing at least one of (a) neurological electrical activity and (b) muscular activity; and
    a processing network adaptively configured for processing conditioned electrical signals derived from muscular activity response differently to electrical signals derived in from neurological electrical activity.

15. The adaptive system according to claim 14 wherein said electrical stimulation signal generator is formed of one or more separate units and each of said units serves a different stimulus modality.

16. The adaptive system according to claim 14 wherein said electrical stimulation signal generator is formed of one or more separate units and each of said units is located to provide to stimulus for a different body location.

17. The adaptive system according to claim 14 wherein said electrical stimulation signal generator is formed of one or more separate units and each of said units serves a different stimulus modality.

18. The adaptive system according to claim 14 wherein said electrical stimulation signal generator is formed of one or more separate units and each of said units is located to provide stimulus for a different body location.

19. The adaptive system according to claim 14, wherein said conditioning network conditions electrical signals representing muscular stimulation activity, and said processing network is adaptively configured for processing conditioned electrical signals derived by neurological electrical stimulation.

20. The adaptive system according to claim 14 wherein said electrical stimulation signal generator is a single electrical stimulation generator for monitoring both neuromuscular transmission monitoring and somatosensory evoked potential.

21. The adaptive system according to claim 14 wherein said electrodes are a single pair of electrodes for monitoring both NMT and SEP signals.

22. The adaptive system according to claim 14 wherein said probes are a single pair of stimulator probes to evoke SEP and NMT either independently or concurrently.

23. The adaptive system according to claim 14 wherein said electrodes coupled to said conditioning network are a single pair of electrodes for monitoring muscle and neurological electrical activity of a patient.

24. An adaptive system for monitoring neurological electrical activity, comprising:
an electrical stimulation signal generator;
a conditioning network for coupling to electrodes and for conditioning electrical signals received via electrodes in response to said electrical stimulation, said electrical signals representing at least one of (a) neurological electrical activity and (b) muscular activity; and
a processing network adaptively configured for processing conditioned electrical signals derived from muscular activity response to differently to electrical signals derived from neurological electrical activity,
wherein adaptive system is adapted to auto-configure itself for at least one of (a) neuromuscular transmission monitoring (b) somatosensory evoked potential stimulation and (c) auditory evoked potential stimulation when connected to an EEG module and to a neuromuscular transmission monitoring device only when not connected to said EEG module.

25. An adaptive system for monitoring neurological electrical activity, comprising:
an electrical stimulation signal generator;
a conditioning network for coupling to electrodes and for conditioning electrical signals received via electrodes in response to said electrical stimulation, said electrical signals representing at least one of (a) neurological electrical activity and (b) muscular activity;
a processing network adaptively configured for processing conditioned electrical signals derived from muscular activity response to differently to electrical signals derived from neurological electrical activity,
a digital serial interface for sending trigger information from an evoked potential stimulator to an EEG device for synchronization with a spontaneous EEG signal.

26. An adaptive system for monitoring neurological electrical activity, comprising:
an electrical stimulation signal generator;
a conditioning network for coupling to electrodes and for conditioning electrical signals received via electrodes in response to said electrical stimulation, said electrical signals representing at least one of (a) neurological electrical activity and (b) muscular activity; and
a processing network adaptively configured for processing conditioned electrical signals derived from muscular activity response to differently to electrical signals derived from neurological electrical activity,
a single trigger line for transmitting a combined time-of-occurrence and ID code therethrough in order to differentiate among different stimulation modes or sites when triggering an EEG device.

27. A method for monitoring neurological electrical activity, the steps comprising:
generating an electrical stimulation signal;
generating an acoustic stimulation signal;
providing a conditioning network for coupling to electrodes and for conditioning electrical signals received via electrodes, said electrical signals representing neurological electrical activity at least partially generated in response to at least one of (a) said electrical muscular stimulation and (b) said acoustic stimulation; and being adaptively configured for processing conditioned electrical signals derived from neurological activity in response to said electrical muscular stimulation differently to electrical signals derived in response to acoustic stimulation.

28. The method according to claim 27 wherein said electrical stimulation signal is generated by an electrical stimulator formed of one or more separate units to each said unit serving a different stimulus modality.

29. The method according to claim 27 wherein said electrical stimulation signal is generated by an electrical stimulator formed of one or more separate units wherein each said unit is located at and provides stimulus for a different body location.

30. The method according to claim 27 wherein said acoustic stimulation signal is generated by an acoustic stimulator unit formed of one or more separate units wherein each said unit serves a different stimulus modality.

31. The method according to claim 27 wherein said acoustic stimulation signal is generated by an acoustic stimulator unit formed of one or more separate units wherein each said unit is located to provide stimulus for a different body location.

32. The method according to claim 27 further comprising the step of conditioning electrical signals representing acoustic stimulation activity, and processing conditioned electrical signals derived by acoustic stimulation.

33. The method according to claim 27 further comprising the step of monitoring both neuromuscular transmission monitoring and somatosensory evoked potential by means of a single electrical stimulation generator circuit.

34. The method according to claim 27 further comprising the step of monitoring both NMT and SEP signals by means of a pair of electrodes.

35. The method according to claim 27 further comprising the step of eliciting SEP or NMT signals either independently or concurrently by means of a single pair of stimulator probes.

36. The method according to claim 27 further comprising the step of monitoring muscle and neurological electrical activity of a patient by means of a single pair of electrodes coupled to a conditioning network.

37. A method for monitoring neurological electrical activity, the steps comprising:
generating an electrical stimulation signal;
generating an acoustic stimulation signal;
providing a conditioning network for coupling to electrodes and for conditioning electrical signals received via electrodes, said electrical signals representing neurological electrical activity at least partially generated in response to at least one of (a) electrical muscular stimulation and (b) said acoustic stimulation; and being adaptively configured for processing conditioned electrical signals derived from neurological activity in response to said electrical muscular stimulation differently to electrical signals derived in response to acoustic stimulation; and automatically configuring said conditioning network for (a) neuromuscular transmission monitoring, (b) somatosensory evoked potential stimulation and (c) auditory evoked potential stimulation when connected to an EEG module and to a neuromuscular transmission monitoring device only when not connected to said EEG module.

38. A method for monitoring neurological electrical activity, the steps comprising:

generating an electrical stimulation signal;

generating an acoustic stimulation signal;

providing a conditioning network for coupling to electrodes and for conditioning electrical signals received via electrodes said electrical signals representing neurological electrical activity at least partially generated in response to at least one of (a) electrical muscular stimulation and (b) said acoustic stimulation; and being adaptively configured for processing conditioned electrical signals derived from neurological activity in response to said electrical muscular stimulation differently to electrical signals derived in response to acoustic stimulation; and sending trigger information through a digital serial interface from an evoked potential stimulator to an EEG device for synchronization with a spontaneous EEG signal.

39. A method for monitoring neurological electrical activity, the steps comprising:

generating an electrical stimulation signal;

generating an acoustic stimulation signal;

providing a conditioning network for coupling to electrodes and for conditioning electrical signals received via electrodes, said electrical signals representing neurological electrical activity at least partially generated in response to at least one of (a) electrical muscular stimulation and (b) said acoustic stimulation; and being adaptively configured for processing conditioned electrical signals derived from neurological activity in response to said electrical muscular stimulation differently to electrical signals derived in response to acoustic stimulation; and transmitting a combined time-of-occurrence and ID code therethrough in order to differentiate among different stimulation modes or sites when triggering an EEG device by means of a single trigger line.

* * * * *